US012714860B2

(12) United States Patent
Robinson et al.

(10) Patent No.: US 12,714,860 B2
(45) Date of Patent: Aug. 25, 2026

(54) WIRELESS MONITORING AND CONTROL OF IMPLANTABLE MAGNETOELECTRIC DEVICES

(71) Applicants: William Marsh Rice University, Houston, TX (US); WTMC Innovation Factory—Motif Neurotech, Houston, TX (US)

(72) Inventors: Jacob T. Robinson, Houston, TX (US); Joshua Woods, Houston, TX (US); Matthew Kuhn, Houston, TX (US); Kaiyuan Yang, Houston, TX (US); Fatima Alrashdan, Houston, TX (US); Zhanghao Yu, Houston, TX (US)

(73) Assignees: William Marsh Rice University, Houston, TX (US); WTMC Innovation Factory—Motif Neurotech, Houston, TX (US)

( * ) Notice: Subject to any disclaimer, the term of this patent is extended or adjusted under 35 U.S.C. 154(b) by 0 days.

(21) Appl. No.: 18/914,049

(22) Filed: Oct. 11, 2024

(65) Prior Publication Data

US 2025/0032797 A1 Jan. 30, 2025

Related U.S. Application Data

(62) Division of application No. 18/632,405, filed on Apr. 11, 2024.

(Continued)

(51) Int. Cl.
*A61N 1/36* (2006.01)
*A61N 1/372* (2006.01)

(52) U.S. Cl.
CPC ....... *A61N 1/36139* (2013.01); *A61N 1/3615* (2013.01); *A61N 1/37223* (2013.01); *A61N 1/37235* (2013.01); *A61N 1/37264* (2013.01)

(58) Field of Classification Search
CPC .............. A61N 1/36139; A61N 1/3615; A61N 1/37223; A61N 1/37235; A61N 1/37264
See application file for complete search history.

(56) References Cited

U.S. PATENT DOCUMENTS 12,377,272 B2 * 8/2025 Schepis .............. A61N 1/36071
2013/0261703 A1 10/2013 Chow et al.

(Continued)

FOREIGN PATENT DOCUMENTS

WO WO-2020206332 A1 * 10/2020 ......... A61N 1/37223
WO WO 2022/192894 9/2022

OTHER PUBLICATIONS

Parastarfeizabadi, Mahboubeh & Kouzani, Abbas. (2017). Advances in closed-loop deep brain stimulation devices. Journal of NeuroEngineering and Rehabilitation. 14. 10.1186/s12984-017-0295-1. (Year: 2017).*

(Continued)

*Primary Examiner* — Jennifer Pitrak McDonald
*Assistant Examiner* — Christopher J Mutchler
(74) *Attorney, Agent, or Firm* — pH IP Law

(57) ABSTRACT

Embodiments disclosed herein generally relate to wirelessly monitoring and controlling implantable magnetoelectric devices. Particularly, aspects of the present disclosure are directed to a system that includes an implantable device, a base station, and one or more sensors that are physically connected or wirelessly connected to the base station. The implantable device includes a magnetoelectric film, an electrical circuit coupled to the magnetoelectric film, and one or more electrodes. The base station includes a magnetic field generator and a magnetic transceiver.

24 Claims, 7 Drawing Sheets

Related U.S. Application Data

(60) Provisional application No. 63/459,360, filed on Apr. 14, 2023.

(56) References Cited

U.S. PATENT DOCUMENTS

| | | | | |
|---|---|---|---|---|
| 2015/0157868 | A1 | 6/2015 | Franke et al. | |
| 2015/0174418 | A1 | 6/2015 | Tyler et al. | |
| 2017/0043167 | A1* | 2/2017 | Widge | A61B 6/037 |
| 2017/0224990 | A1* | 8/2017 | Goldwasser | A61N 1/0476 |
| 2018/0304086 | A1* | 10/2018 | Shellhammer | A61B 5/7221 |
| 2018/0353095 | A1* | 12/2018 | Boesen | A61B 5/291 |
| 2020/0001089 | A1 | 1/2020 | Chae | |
| 2022/0029465 | A1 | 1/2022 | Nielsen et al. | |
| 2022/0168579 | A1 | 6/2022 | Robinson et al. | |
| 2022/0346698 | A1* | 11/2022 | Esteller | A61N 1/36139 |
| 2023/0144885 | A1 | 5/2023 | Zhang et al. | |
| 2023/0226358 | A1* | 7/2023 | Lebaron | A61N 1/36114 607/62 |
| 2023/0277059 | A1 | 9/2023 | Lucey et al. | |
| 2023/0405340 | A1 | 12/2023 | Robinson et al. | |
| 2024/0041399 | A1 | 2/2024 | Pivonka et al. | |
| 2024/0342484 | A1* | 10/2024 | Robinson | A61N 1/36139 |
| 2024/0363218 | A1* | 10/2024 | Robinson | A61N 1/36139 |
| 2024/0374893 | A1* | 11/2024 | Robinson | A61N 1/0551 |

OTHER PUBLICATIONS

Z. Yu et al., “34.3 An 8.2mm3 Implantable Neurostimulator with Magnetoelectric Power and Data Transfer,” 2020 IEEE International Solid-State Circuits Conference—(ISSCC), San Francisco, CA, USA, 2020, pp. 510-512, doi: 10.1109/ISSCC19947.2020.9062931. (Year: 2020).*

PCT International Search Report and Written Opinion issued in International Application No. PCT/US2024/023962, mailed Mar. 19, 2025.

Office Action issued in U.S. Appl. No. 18/632,405, mailed Aug. 30, 2024.

Office Action issued in U.S. Appl. No. 18/632,405, mailed Oct. 24, 2024.

Office Action issued in U.S. Appl. No. 18/632,405, mailed Feb. 12, 2025.

Office Action issued in U.S. Appl. No. 18/632,405, mailed Sep. 5, 2025.

PCT International Search Report and Written Opinion issued in International Application No. PCT/US2025/044612, mailed on Oct. 29, 2025.

International Preliminary Report on Patentability issued in International Application No. PCT/US2024/023962, mailed on Oct. 8, 2025.

Office Action issued in U.S. Appl. No. 18/632,405, mailed Apr. 27, 2026. (32 Pages).

* cited by examiner

WIRELESS MONITORING AND CONTROL OF IMPLANTABLE MAGNETOELECTRIC DEVICES

CROSS-REFERENCE OF RELATED APPLICATIONS

This application is a divisional of U.S. application Ser. No. 18/632,405, filed Apr. 11, 2024, which claims priority to U.S. Provisional Application No. 63/459,360, filed Apr. 14, 2023, titled "WIRELESS MONITORING AND CONTROL OF IMPLANTABLE MAGNETOELECTRIC DEVICES", each of which is incorporated by reference in its entirety for all purposes.

STATEMENT REGARDING FEDERALLY SPONSORED RESEARCH AND DEVELOPMENT

This invention was made with government support under Grant No. ECCS-2023849 awarded by the National Science Foundation and Grant No. FA8650-21-2-7110 awarded by the Air Force Research Laboratory. The government has certain rights in the invention.

FIELD

The present disclosure relates to implantable devices, and, in particular, to techniques for transmitting data wirelessly between implantable magnetoelectric devices.

BACKGROUND

Wireless implantable bioelectronics provide hope for revolutionary clinical therapies, such as treating neurological and psychiatric disorders by interfering directly with the nervous system. These devices can deliver controlled stimulation to modulate the electrical activities of the nervous system and/or record electrical, chemical, and physical properties for better diagnosis.

One challenge in the design of wireless bio-implants is to reliably power and communicate with miniaturized implants. While batteries have been the conventional power source of medical implants for a long time, the last decade has seen a transition to wireless power transfer solutions that feature smaller footprints, less weight, longer lifetime, and less invasive implantation procedures. Various wireless power transfer technologies (e.g., including radio frequency (RF), inductive coupling, ultrasound, and light) have demonstrated the ability to wirelessly power medical implants. However, these wireless power transfer technologies face trade-offs between receiver size and misalignment tolerance, transmission loss, and/or power that can safely be delivered through the biological tissues. Accordingly, improvements for miniaturized wireless bio-implants for advanced biomedical applications like closed-loop neuromodulation are desirable.

SUMMARY

In some embodiments, a system is provided. The system can include an implantable device that includes a magnetoelectric film, an electrical circuit coupled to the magnetoelectric film, and one or more electrodes. The system can also include a base station that includes a magnetic field generator and a magnetic transceiver. The system can also include one or more sensors that are physically connected or wirelessly connected to the base station. For example, a sensor of the one or more sensors may be physically connected to the implantable device and may be wirelessly connected to the base station (e.g., via one or more components of the implantable device, such as the magnetic field generator and/or the magnetic transceiver).

In some embodiments, the base station further includes electronics configured to record one or more stimulation times at which the implantable device delivers stimulation to a target tissue, access a physiological signal collected by the one or more sensors, identify one or more select portions of the physiological signal, where each portion has a start time corresponding to a stimulation time of the one or more stimulation times, facilitate a prediction of, based on the one or more select portions, whether or a degree to which an implant stimulation protocol is resulting in a target effect, and facilitate a modification of the implant stimulation protocol based on the prediction. The predicting of whether or the degree to which an implant stimulation protocol may be performed using the electronics, may be performed automatically, and/or may be performed in response to input received from a user of a computing system (e.g., to which one or more signals, results, recommendations, disclosed result(s), and/or disclosed output(s) are received and/or output.

In some embodiments, modifying the implant stimulation protocol can include setting a new schedule as to when the implantable device delivers stimulation.

In some embodiments, modifying the implant stimulation protocol can include identifying a new intensity for stimulation that is generated by the implantable device.

In some embodiments, the electronics can be further configured to access a secondary signal collected by an input component of the base station and identify one or more select portions of the secondary signal. Each portion has a start time relative to a stimulation time of the one or more stimulation times. The prediction of whether or the degree to which the implant stimulation protocol is resulting in the target effect can be further based on the one or more secondary select portions.

In some embodiments, the secondary signal was generated based on backscattering of a magnetic field applied by the magnetic field generator of the base station.

In some embodiments, the system includes a wearable component that includes the base station and the one or more sensors.

In some embodiments, the wearable component is configured to be worn on a head of a user.

In some embodiments, the wearable component is configured to be worn on around a waist of a user.

In some embodiments, the wearable component is configured to be worn on around a neck of a user.

In some embodiments, the one or more sensors includes at least one electroencephalography (EEG) electrode.

In some embodiments, the one or more sensors include a heart-rate monitor, an accelerometer, and/or an optode.

In some embodiments, the electrical circuit can further include a resonant frequency modulator configured to modulate the resonant frequency of the magnetoelectric film by applying different electric loading conditions that change a property of the magnetoelectric film.

In some embodiments, the implantable device can be configured to detect an activation field and establish a bi-directional communication link with the base station when the base station is positioned proximate to the implantable device.

In some embodiments, a method is provided. The method can involve sending, by electronics of a base station including a magnetic field generator and a magnetic transceiver, instructions including an implant stimulation protocol to an implantable device for delivering stimulation to a target tissue at one or more stimulation times. The implantable device includes a magnetoelectric film, an electric circuit coupled to the magnetoelectric film, and one or more electrodes. The method can further involve recording the one or more stimulation times at which the implantable device delivers the stimulation to the target tissue, accessing a physiological signal collected by one or more sensors that are physically connected or wirelessly connected to the base station, identifying one or more select portions of the physiological signal, where each portion has a start time corresponding to a stimulation time of the one or more stimulation times, facilitating a prediction of, based on the one or more select portions, whether or a degree to which the implant stimulation protocol is resulting in a target effect, and facilitate a modification of the implant stimulation protocol based on the prediction.

In some embodiments, modifying the implant stimulation protocol includes setting a new schedule as to when the implantable device delivers stimulation.

In some embodiments, modifying the implant stimulation protocol includes identifying a new intensity for stimulation that is generated by the implantable device.

In some embodiments, the method further involves accessing a secondary signal collected by an input component of the base station and identifying one or more secondary select portions of the secondary signal. Each secondary select portion has a start time relative to a stimulation time of the one or more stimulation times. The prediction of whether or the degree to which the implant stimulation protocol is resulting in the target effect can be further based on the one or more secondary select portions.

In some embodiments, the secondary signal was generated based on backscattering of a magnetic field applied by the magnetic field generator of the base station.

In some embodiments, the one or more sensors includes at least one electroencephalography (EEG) electrode.

In some embodiments, the one or more sensors includes a heart-rate monitor, an accelerometer, and/or an optode.

In some embodiments, the method further involves modulating, by a resonant frequency modulator of the base station, a resonant frequency of the magnetoelectric film by applying different electric loading conditions that change a property of the magnetoelectric film.

In some embodiments, the implantable device is configured to detect an activation field and establish a bi-directional communication link with the base station when the base station is positioned proximate to the implantable device.

In some embodiments, the method further involves accessing a diagnostic signal of the implantable device during the one or more stimulation times at which the implantable device delivers the stimulation to the target tissue and modifying the implant stimulation based on the diagnostic signal.

In some embodiments, a method is provided. The method can involve sending, by electronics of a base station including a magnetic field generator and a magnetic transceiver, instructions including an implant stimulation protocol to a first implantable device for delivering stimulation to a target tissue at one or more stimulation times. The first implantable device includes a first magnetoelectric film, a first electric circuit coupled to the first magnetoelectric film, and one or more first electrodes. The method involves recording, by a second implantable device, the one or more stimulation times at which the first implantable device delivers the stimulation to the target tissue. The second implantable device includes a second magnetoelectric film, a second electric circuit coupled to the second magnetoelectric film, and one or more second electrodes. The method involves accessing a physiological signal collected by one or more sensors that are physically connected or wirelessly connected to the base station, identifying one or more select portions of the physiological signal, where each portion has a start time corresponding to a stimulation time of the one or more stimulation times, facilitate a prediction of, based on the one or more select portions, whether or a degree to which the implant stimulation protocol is resulting in a target effect, and facilitate a modification of the implant stimulation protocol based on the prediction.

Some embodiments of the present disclosure include a system including one or more data processors. The system can further include a non-transitory computer readable storage medium containing instructions which, when executed on the one or more data processors, cause the one or more data processors to perform part or all of one or more of the methods disclosed herein.

In some embodiments, a computer-program product is provided that is tangibly embodied in a non-transitory machine-readable storage medium. The computer-program product can include instructions configured to cause one or more data processors to perform part or all of one or more of the methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

Aspects and features of the various embodiments will be more apparent by describing examples with reference to the accompanying drawings, in which.

Figure 1:
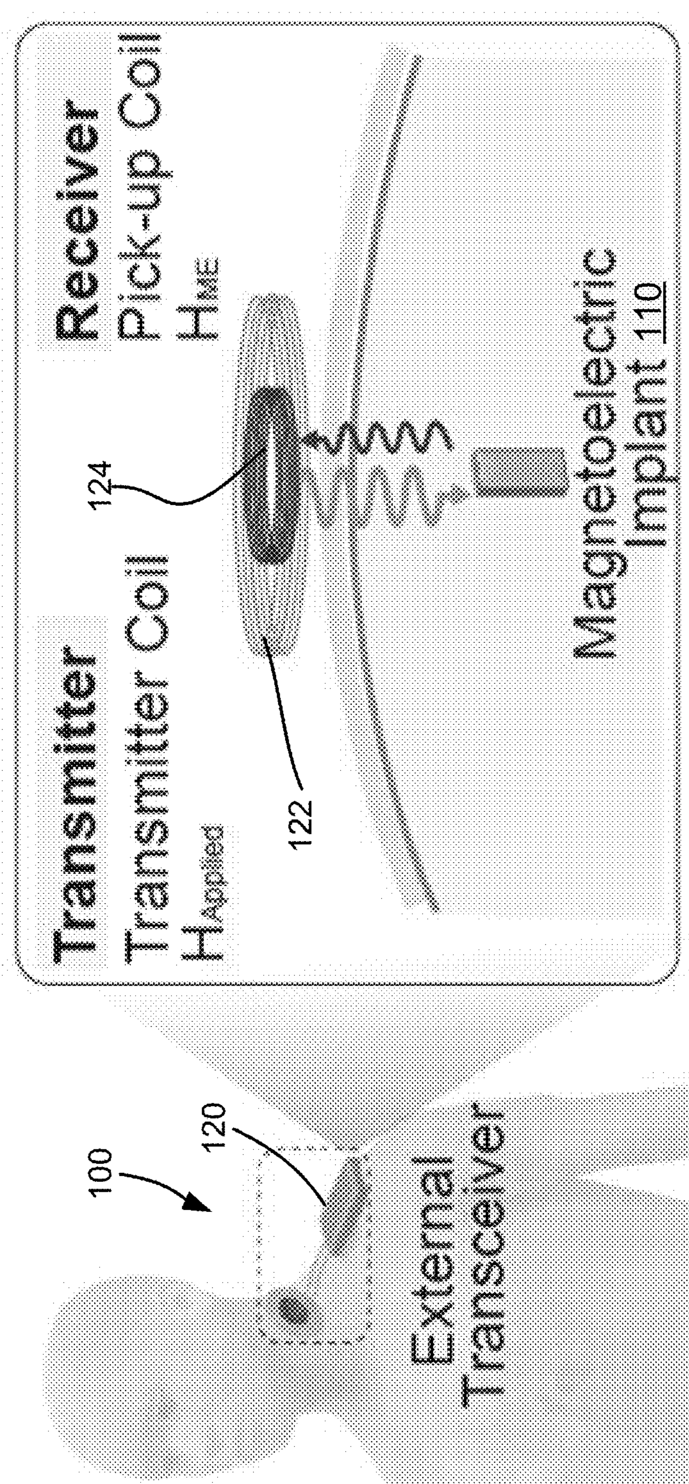
FIG. 1 illustrates an exemplary system including an implantable device and a base station according to some aspects of the present invention.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

While certain embodiments are described, these embodiments are presented by way of example only, and are not intended to limit the scope of protection. The apparatuses, methods, and systems described herein may be embodied in a variety of other forms. Furthermore, various omissions, substitutions, and changes in the form of the example methods and systems described herein may be made without departing from the scope of protection.

Implantable devices can be used to provide stimulation to the brain, or other nervous system regions, of subjects. The stimulations may be used (for example) to treat a medical condition (e.g., a neurological or psychiatric disorder) or a symptom. These implantable devices are typically on the mm-scale and usually require carrier frequencies of more than a GHz. Unfortunately, stimulation at such high carrier frequencies can increase the possibility of the body not responding to the stimulation. Inductive coupling has been used in wireless implantable systems because of its flexible capability for charging and bi-directional telemetry. However, the coupling is sensitive to the variations in distance and direction, especially when the implant coil is small. Additionally, most inductively powered devices work at 13.56 MHz or higher frequencies for better power transmission efficiency, but such a frequency can result in substantial energy being absorbed by the body, which may be undesirable. As a result, inductively powered devices may be required to operate under certain restrictions, such as time restrictions for how often and how long these devices can be operated at a particular frequency within a particular time period. While ultrasound and optics have shown potentials in wirelessly transmitting power and data, they suffer from energy loss due to reflection or scattering when transferring through different tissue layers, limiting their efficiency.

Embodiments of the present disclosure utilize magnetoelectric power for wirelessly powering mm-sized devices implanted deep inside the body by converting low-frequency (e.g., hundreds of kHz) magnetic fields to electric voltage using magnetoelectric transducers. Systems and methods that use magnetoelectric power results in several advantages (e.g., relative to RF, inductive coupling, ultrasound, and light power transfer techniques) including high power transmission efficiency with miniaturized size, high power delivery (e.g., greater than 1 mW), and high misalignment tolerance (e.g., angle offset and lateral offset) relative to inductive coupling and ultrasound power transfer devices. These features are empowered by using magnetoelectric materials that have sufficient power density, mechanical resonance frequency, and permeability to concentrate magnetic flux inside the material. First, the magnetoelectric transducer's voltage coefficient is independent of the transducer's width and length. As a result, the magnetoelectric effects can support miniaturization of an implantable device while maintaining a power transfer efficiency that is higher than the power transfer efficiency of radio frequency, inductive coupling, and ultrasound power transfer devices. In addition, the permeability of magnetostrictive materials can result in significant concentration of magnetic flux, which enhances the magnetoelectric power transfer's robustness to misalignment. Magnetoelectric communication is also less sensitive to angles and lateral offsets than ultrasound-based wireless transfers that require focused sound waves. Additionally, the sub-MHz low resonance frequency of magnetoelectric leads to lower tissue absorption, and a stronger magnetic field is allowed without violating safety limits. The use of magnetoelectric power results in an order-of-magnitude higher power that can be safely delivered to the implants deep inside the body compared to high-frequency inductive coupling or RF. Specifically, a magnetoelectric implantable device working at the 335-kHz resonance frequency may be able to receive a peak power of 3.8 mW at 3 cm under electromagnetic exposure limits, which is equivalent to 0.4 mW for the 13.56-MHz inductive coupling counterpart.

In some embodiments, the implantable device can include a magnetoelectric film that acts as a transducer, an electrical circuit (e.g., an application-specific integrated circuit (ASIC) chip), and one or more electrodes. A base station in communication with the implantable device can provide wireless power transfer and data downlink communication to the implantable device. Sharing the same magnetoelectric mechanism for wireless power and communication can facilitate miniaturization of the implantable device and improve power transfer efficiency and data transfer efficiency. The base station can include a magnetic field generator that acts as a magnetoelectric transmitter to the implantable device to digitally program stimulation parameters of an implant stimulation protocol. Uplink communications may be useful for the implantable device to report sensor data for closed-loop applications and to monitor and calibrate operation conditions of the implantable device. Magnetoelectric backscatter can be used to send data from the implantable device to a magnetic transceiver of the base station. One or more sensors (e.g., electroencephalogram (EEG) electrodes, heart-rate monitors, accelerometers, or optodes such as functional near-infrared spectroscopy (fNIRS) sensors) can also be physically connected or wirelessly connected to the base station for monitoring physiological conditions of a user. In some instances, a sensor of the one or more sensors is an electronic biopotential sensor, which may be part of or physically connected with and/or part of the implantable device.

Physiological signals generated, captured and/or communicated by the sensors, and optionally from the implantable device, may be used to predict whether or a degree to which the implant stimulation protocol is resulting in a target effect. The implant stimulation protocol may then be modified based on the prediction (e.g., based on rules defining stimulation parameters that are associated with particular values for variables of the physiological signal and/or the signal generated by the implantable device). Accordingly, the implantable device and the base station can have bi-directional communication that allows for tuning of stimulation parameters based on a user's response to a particular implant stimulation protocol.

II. Example Systems

FIG. 1 illustrates an exemplary system 100 including an implantable device 110 and a base station 120 according to some aspects of the present invention. Using magnetoelectric communication, a transmitter coil 122 of the base station 120 can modulate a magnetic field applied to the implantable device 110. The transmitter coil 122 may be a magnetic field generator. Modulating the electric load leads to magnetoelectric resonance frequency changes for frequency-shift-keying (FSK) modulation. A resonant frequency modulator of an electrical circuit of the implantable device 110 can implement capacitive load shifting to maximize the resonance frequency change without substantial fluctuations of received voltage. Magnetostriction effects can be leveraged for uplink communication using magnetoelectric backscatter received by a pick-up coil 124 of the base station 120. The pick-up coil 124 may be a magnetic transceiver. In an example, the implantable device 110 can integrate a 1×1.5-$mm^2$ ASIC chip, a 2×5×0.28-$mm^3$ magnetoelectric film, a 0.25-$mm^3$, 22-μF energy storage capacitor, and 1-$mm^2$ onboard electrodes within an 8.2-$mm^3$ volume. In other cases, the uplink communication may be achieved with radio frequency (RF), near field communication (NFC), Bluetooth, or optical communication.

The magnetoelectric film of the implantable device 110 can be fabricated using a bilayer or trilayer sheet including one or more magnetostrictive layers and one or more piezoelectric layers. In an example, the magnetostrictive layer can use 27-μm Metglas, and the piezoelectric layer can use 254-μm-thick lead zirconium titanate PZT-5 material. When the transmitter coil 122 applies an external magnetic field, mechanical vibrations are generated in the magnetostrictive layer due to the Joule effect. Since the magnetostrictive layer and the piezoelectric layer are mechanically coupled, these vibrations are transferred to the piezoelectric layer to create an electric potential across the magnetoelectric film due to the direct piezoelectric effect.

The vibrations generated in the magnetostrictive layer result in a change in the material magnetization due to the Villari effect. This change can be seen as a backscattered field generated by the magnetoelectric film. Hence, utilizing these echoes as backscattered signals can enable uplink data transfer from the implantable device 110 to the pick-up coil 124. During the on-time of the applied magnetic field, the magnetoelectric materials vibrate at the applied field frequency. Since the generated backscattered field may oscillate at the same excitation frequency, it may be challenging to decouple the applied field frequency signal from the backscattered signal. To isolate the response of the magnetoelectric film, the backscattered field can be measuring during a ring-down period when the excitation field is off. Over the ring-down period, the magnetoelectric film dissipates the stored mechanical energy in the form of decaying voltage at its mechanical resonance frequency irrespective of the excitation field frequency.

In some examples, characteristics of the backscattered field can be changed at the implantable device 210 to modulate the backscattered signal for transmitting data. Although the backscattered field is generated by the magnetostrictive layer, modulating the characteristics of either the piezoelectric layer, magnetostrictive layer, or both can affect the backscattered field due to the mechanical coupling of the layers. The modulation of the backscattered field can be done by controlling the effective mechanical, magnetic, or electric properties of the composite. In an example, the magnetostrictive materials can be coated with a thin layer of stimuli-responsive polymers that respond to external stimuli by shifting the overall mass and mechanically modulating the resonance frequency of the magnetoelectric film. The resonant frequency modulator can modulate the resonant frequency of the magnetoelectric film by applying different electrical loading conditions that change a property of the magnetoelectric film. In some instances, an electric loading modulation technique can be used to tune the characteristics of the backscattered field. The electric load can be either an active load (e.g., a direct current (DC) biasing voltage) or a passive load (e.g., inductive, resistive, capacitive, or a combination thereof). Using passive loads may enable a miniaturized footprint of the implantable device 110 and limit constraints on the power budget.

Changing the capacitive or resistive loads across the magnetoelectric film can change the voltage across the magnetic film as well as its resonance frequency. Consequently, the amplitude and frequency of the backscattered field during the ring-down period are changed. Since a frequency shift may be more immune to the depth variation and misalignment that often occur during implantation of an implantable device, frequency modulation can be used to encode uplink data of the implantable device 110.

Capacitive load-shift-keying (LSK) modulation can result in a large frequency shift and small voltage drop to help resolve the frequency difference at the pick-up coil 124 and to improve the signal-to-noise ratio (SNR). The LSK-induced frequency-shift keying (FSK) can be used to digitally encode the data by switching between two load conditions: an open circuit and a capacitive load. To determine the suitable capacitive load to be implemented on the ASIC chip, the resonance frequency of the magnetoelectric film can be measured while connected in parallel to different capacitive loads and compared with that a mathematical model for validation.

Figure 2:
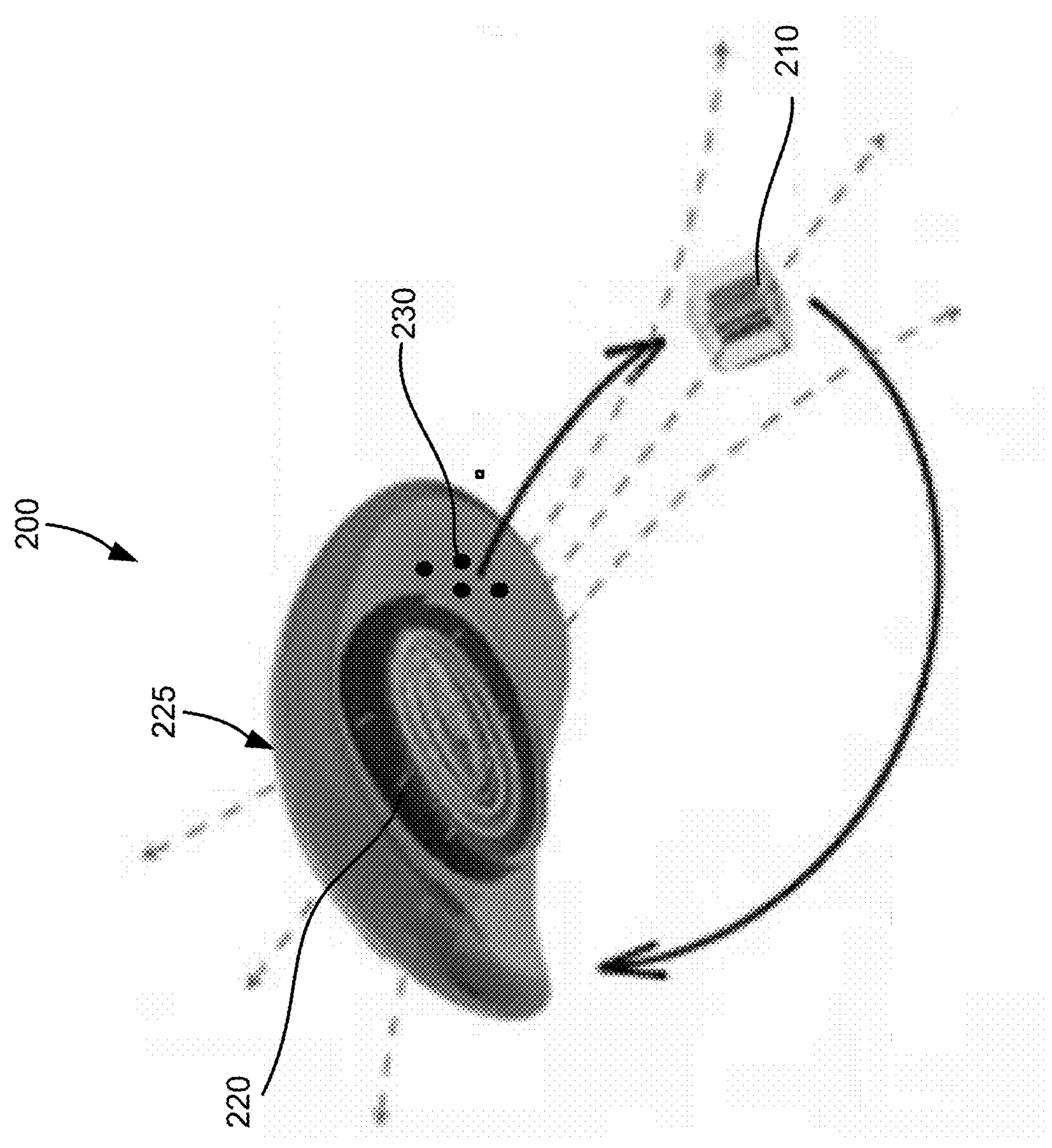
FIG. 2 illustrates an exemplary wearable device including a base station and sensors for communicating with an implantable device according to some aspects of the present invention.

FIG. 2 illustrates an exemplary wearable component 225 including a base station 220 and sensors 230 for communicating with an implantable device 210 according to some aspects of the present invention. The wearable component 225 can be part of a system 200 that includes the implantable device 210, the base station 220, and the sensors 230. The wearable component 225 is illustrated in FIG. 2 as being a headband that can be worn on a head of a user. In such examples, the implantable device 210 can be implanted in a brain of the user. For instance, the implantable device 210 may be implanted between 1 and 6 cm deep in the brain in a target region. The target region may be based on a condition or disorder of the user. For instance, the target region associated with providing stimulation to treat depression may be a different target region than is associated with providing stimulation to treat Parkinson's. One session of a therapeutic pulse sequence can range from 1 minute to 120 minutes of therapy consisting of continuous stimulation at a fixed frequency (e.g., 10 Hz or 130 Hz) a continuous series of bursts (e.g., "continuous theta burst stimulation (cTBS)": three pulses at 50 Hz repeated every 200 ms), or a pattern of bursts (e.g., "intermittent theta burst stimulation (iTBS)": three pulses at 50 Hz repeated every 200 ms for 2 seconds, repeated every 10 seconds). In all cases, the number of therapeutic sessions can be repeated multiple times per day with a time between therapies ranging from a few minutes to several hours. For the treatment of depression, the target region may be a dorsolateral prefrontal cortex, whereas for the treatment of Parkinson's, the target region may be the bilateral motor cortex or subthalamic nucleus.

The base station 220 can include electronics for controlling and monitoring stimulation provided to the user by the implantable device 210. The base station 220 may power and communicate with the implantable device 210 using magnetoelectric techniques, as described in FIG. 1. The implantable device 210 can execute an implant stimulation protocol based on instructions received from the electronics. The implant stimulation protocol may be a default implant stimulation protocol, or the base station 220 may receive an indication of the implant stimulation protocol from a user device associated with a clinician, the user, or other personnel. The implant stimulation protocol can indicate an amplitude (e.g., between 0.2 and 3.5 V), shape (e.g., bi-phasic or mono-phasic), pulse width (e.g., between 0.05 and 1.5 ms), and frequency (e.g., between 0 and 500 Hz) for the stimulation. In addition to therapeutic stimulation, the implant stimulation protocol may additionally include diagnostic stimulation that is applied between therapeutic pulse sequences. For instance, if the therapeutic stimulation is the iTBS sequence, diagnostic stimulation can be delivered during the "off periods" of the therapeutic stimulation. The electronics can then record stimulation times at which the implantable device 210 delivers the stimulation to the target tissue.

Although not illustrated in FIG. 2, the system 200 may also include a user device (e.g., smart phone, laptop computer, desktop computer, etc.) that is in communication with the sensors 230 and/or the base station 220. The user device may act as a coordinating hub between the base station 220 and the sensors 230. So, the sensors 230 may be in direct communication with the base station 220, or the sensors 240 may be in indirect communication with the base station 220 via the user device. As an example, the user device may indicate to the base station 220 times at which the sensors 230 should record. The base station 220 can then send instructions to the sensors 230 about when to record. In addition, the sensors 230 may send recorded data to the base station 220 and/or the user device. Indirect communication may include a scenario in which signals from one or more sensors 230 are communicated to and/or availed to a first other component of the implantable device 210, and the first component of the implantable device 210 or a second component of the implantable device 210 then transmits the signals (or a processed version thereof) to the base station 220. Any such processing may be performed using mechanical and/or electronic components. For example, the implantable device 210 may include (for example) electronics, a processor and/or a circuit board that translates signals detected by at least one of the one or more sensors 230 into a processed version thereof. Such processing may include (for example) filtering (e.g., using a bandpass filter, a high-pass filter, a low-pass filter, etc.), performing a classification (e.g., to predict whether a signal exhibits one or more predefined signal characteristics), and/or predicting whether a signal includes one or more given signal features (e.g., that matches or associated with that of a template to at least a threshold amount).

In some examples, multiple implantable devices may be implanted into the brain of the user. Each implantable device may be associated with a different implant stimulation or recording protocol. So, a first implantable device may execute a first implant stimulation protocol of an amplitude of 1.5 V with a mono-phasic shape and a pulse width of 0.5 ms at a frequency of 50 Hz, while a second implantable device executes a second implant stimulation protocol of an amplitude of 1.5 V with a mono-phasic shape and a pulse width of 0.5 ms at a frequency of 100 Hz. Alternatively, a first implantable device may be used to deliver stimulation according to the implant stimulation protocol, whereas a second implantable device may be used to record during the stimulation times of the first implantable device.

Each of the implantable devices may transmit data back to the base station 220. The data uplink may be in the form of a magnetic field generated by each of the implantable devices oscillating at a resonant frequency of the implantable device. The implantable devices can emit electrical signals with different timings or frequencies such that the signals constructively interfere to stimulate the target region. The interference may be created by an overlap between alternating electric fields at the same frequency produced by the multiple implantable devices. Alternatively, the interference may be created by the overlap between alternating electric fields of different frequencies produced by the multiple implantable devices.

In some instances, each implantable device may be controlled by a separate base station. Alternatively, each implantable device may be associated with a unique digital identifier that the base station 220 can use to communicate with the desired implantable device. The unique digital identifier can be a bit sequence in front of a signal. So, the base station 220 can send instructions for the different implant stimulation protocols to the implantable device 210 and additional implantable devices with the appropriate digital identifiers. As an example, the base station 220 can send instructions of the implant stimulation protocol for the implantable device 210 with the unique digital identifier of the implantable device 210. The base station 220 can also send instructions of other implant stimulation protocols for other implantable devices with other digital identifiers. Each of the implantable devices may receive each of the instructions, but may only process and execute the instructions with their corresponding digital identifier. The interference may be produced by controlling a relative timing of the electrical field produced by the implantable devices. So, the implantable device 210 may be instructed to deliver stimulation 10 ms from receiving the instructions and another implantable device may be instructed to deliver stimulation 20 ms from receiving the instructions.

In some examples, the electronics accesses a physiological signal collected by the sensors 230, which may be electrical sensors or optical sensors. For instance, the sensors 230 may be EEG electrodes or optodes (e.g., fNIRS sensors). The physiological signal collected can be based on the type of sensors. For instance, EEG electrodes may measure electrical activity (e.g., beta-band frequency), fNIRS sensors may measure changes in blood flow or oxygenation, accelerometers may measure tremor or seizure activity. The electronics can process the physiological features and/or can facilitate determining whether to record physiological signals, when to record physiological signals and/or how to align physiological signals (e.g., by defining event times that are or may be used for subsequent alignment). Such processing may include (for example) identifying portions of the physiological signal that have a start time corresponding to a stimulation time of the stimulation times at which the implantable device 210 delivers the stimulation. For example, the electronics may determine the start times of the stimulations based on the implant stimulation protocol and then detect the portions of the physiological signal that correspond to the start times. For example, the stimulation may be timed to start according to the phase of the user's natural brain oscillation (e.g., theta band oscillations) as measured by the external EEG or the implantable device 210. As another example, based on the portions of the physiological signal, the electronics can predict whether or a degree to which the implant stimulation protocol is resulting in a target effect. In the case of Parkinson's, the target effect may be a reduction of tremors (e.g., as detected using an accelerometer in a user device) or a reduction in beta band activity (e.g., as detected using a sensor within or connected to the implantable device or in another implantable device or external sensor-such as an EEG device). A particular physiological status (e.g., neural activity, oxygenation level, etc.) may be indicative of the implant stimulation protocol resulting in the target effect. So, if the portions of the physiological signal indicate the particular physiological status for the user, the electronics can determine that the implant stimulation protocol is resulting in the target effect.

The electronics can then modify the implant stimulation protocol based on the prediction of whether or the degree to which the implant stimulation protocol results in the target effect. For instance, a new schedule may be set for when the implantable device 210 delivers the stimulation. The new schedule may be that, rather than stimulation being delivered for one minute at ten-minute intervals, the stimulation is to be delivered for thirty seconds at ten-minute intervals. Additionally or alternatively, modifying the implant stimulation protocol may involve identifying a new intensity for the stimulation that is generated by the implantable device 210. For example, the amplitude may be adjusted from 1.0 V to 2.3 V.

The electronics may determine the implant stimulation protocol or modifications for the implant stimulation profile based on one or more rules. For instance, rules may be configured to include one or more if/then assessments, an equation that calculates one or more stimulation parameters based on variables of the physiological signal or the implant signal, etc. As an example, the if/then assessments may specify that if the physiological signal indicates first neural activity, then the implant stimulation protocol should include an amplitude of 1.0 V, whereas if the physiological signal indicates second neural activity, then the implant stimulation protocol should include an amplitude of 2.3 V. For example, if the stimulus is not generating sufficient changes in the positive or negative local field potential (LFP) or EEG signals following the stimulus, the amplitude can be increased to recruit a stronger neural response. The equation can receive the physiological signal, the implant signal, and/or additional variables and calculate the stimulation parameters. The rules may be defined at least in part by a care physician or other provider.

In an example, the electronics may additionally access a secondary signal collected by an input component of the base station 220. The input component may be a magnetic transceiver or another component. The secondary signal may be generated based on magnetoelectric backscattering, or other uplink modalities, as previously described in FIG. 1. Backscattered signals generated by the implantable device 210 and additional implantable devices may include the unique digital identifiers of the implantable devices. As such, the base station 220 can de-multiplex backscattered signals received from each of the implantable devices. Portions of the secondary signal that have a start time relative to a stimulation time of the implantable device 210 may be identified. For example, the electronics may determine the start times of the stimulations based on the implant stimulation protocol and then detect the portions of the secondary signal that correspond to the start times. The prediction of whether or the degree to which the implant stimulation protocol is resulting in the target effect can be further based on the portions of the secondary signal. So, the implant stimulation protocol may be modified based on the prediction associated with the secondary signal.

The electronics may additionally or alternatively access a diagnostic signal of the implantable device during the one or more stimulation times at which the implantable device 210 delivers the stimulation to the target tissue. The diagnostic signal may indicate one or more properties of the implantable device 210. For instance, the diagnostic signal may indicate an impedance of the electrodes of the implantable device 210. The prediction of whether or the degree to which the implant stimulation protocol is resulting in the target effect can be further based on the diagnostic signal. So, the implant stimulation protocol may be modified based on the prediction associated with the diagnostic signal. As an example, if the diagnostic signal indicates that the impedance of the electrodes changes, the implant stimulation protocol may be modified to increase the amplitude of the stimulation.

Figure 3:
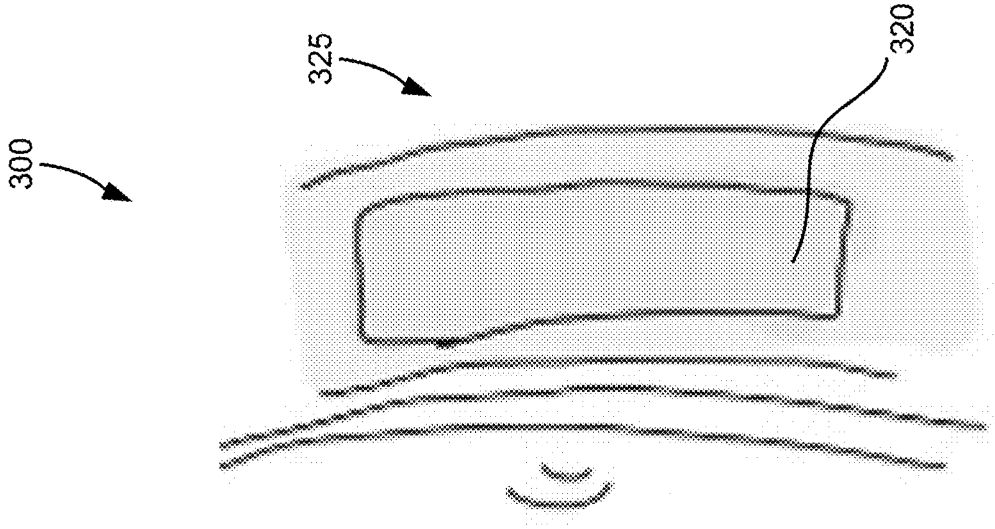
FIG. 3 illustrates another exemplary wearable device including a base station and sensors for communicating with an implantable device according to some aspects of the present invention.
Figure 3:
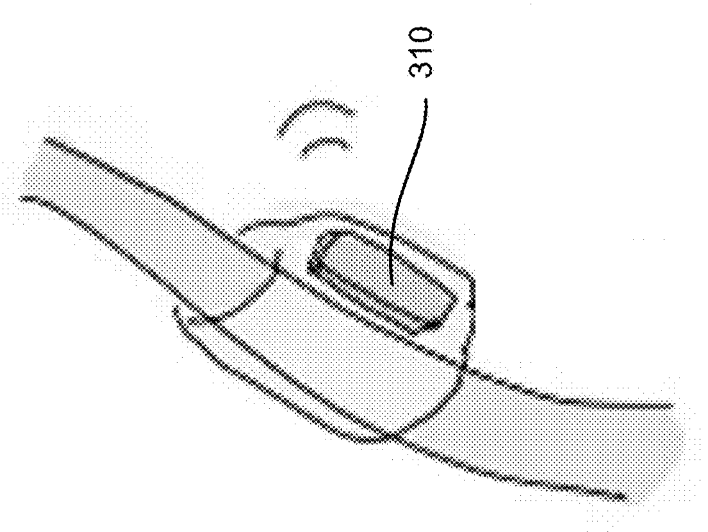

FIG. 3 illustrates another exemplary wearable component 325 including a base station 320 and sensors for communicating with an implantable device 310 according to some aspects of the present invention. The wearable component 325 can be part of a system 300 that includes the implantable device 310, the base station 320, and the sensors 330. The wearable component 325 in FIG. 3 may be a belt that can be worn around a waist of a user. Other wearable components may be worn around a head or neck of the user. The implantable device 310 can be in a cuff that surrounds a nerve (e.g., vagus nerve or pelvic parasympathetic nerves) of a target region of the user.

In an example, the implantable device 310 can be used to stimulate afferent and efferent peripheral nerve targets in the abdominal cavity of the user to deliver therapeutic stimulation to elicit target organ function or block or modify disease-causing communication from the target organ to the central nervous system. Due to the small size of the implantable device 310, the risk of bowel perforation may be reduced by using the implantable device 310 compared to other implantable devices that use alternate power transfer techniques (e.g., inductive coupling, ultrasound, light, etc.). Peripheral nerves may be stimulated to control insulin function, bile production, stomach fullness and appetite indicators, bladder control, bowel control, sexual function, etc.

The base station 320 can include electronics for controlling and monitoring stimulation provided to the user by the implantable device 310, similar to the base station 220 in FIG. 2. The base station 320 may power and communicate with the implantable device 310 using magnetoelectric techniques, as described in FIG. 1. The implantable device 310 can execute an implant stimulation protocol based on instructions received from the electronics. For instance, the implant stimulation protocol can indicate an amplitude (e.g., between 0.2 and 3.5 V), shape (e.g., bi-phasic or mono-phasic), pulse width (e.g., between 0.05 and 1.5 ms), and frequency (e.g., between 0 and 200 Hz) for the stimulation. The electronics can then record stimulation times at which the implantable device 310 delivers the stimulation to target tissue, determine whether the implant stimulation protocol is resulting in a target effect, and modify the implant stimulation protocol based on the prediction. The prediction and modification of the implant stimulation protocol may similarly be based on backscattered signals received by the base station 320 from the implantable device 310.

Figure 4:
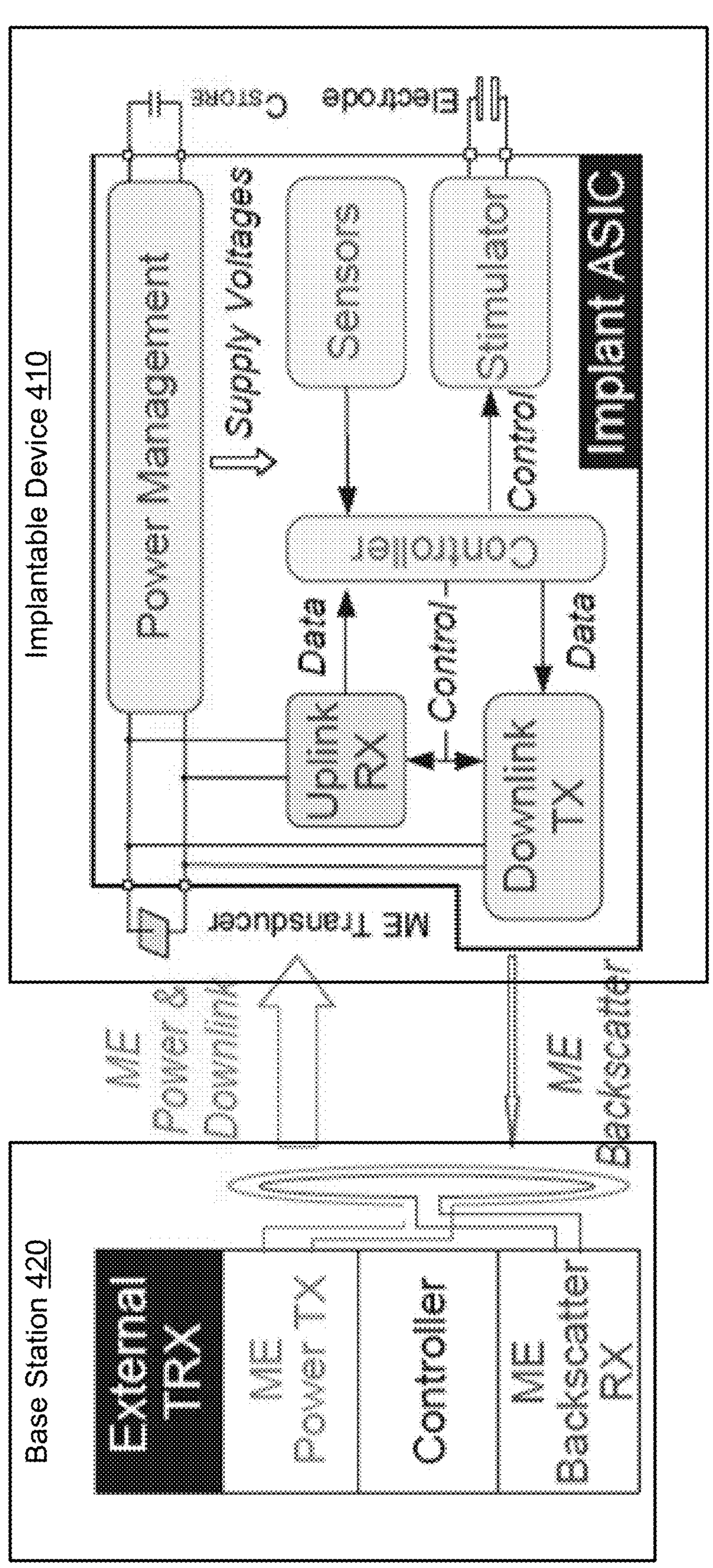
FIG. 4 illustrates exemplary electronics of a base station and an implantable device 410 according to some aspects of the present invention.

FIG. 4 illustrates exemplary electronics of a base station 420 and an implantable device 410 according to some aspects of the present invention. The implantable device 410 wirelessly receives power to generate power supplies, communicates with a magnetic transceiver of the base station 420, senses the received voltage and an ambient temperature, and delivers programmable electrical stimulus. The magnetic transceiver includes a power transmitter, a backscatter receiver, and a controller. The power transmitter connects a coil to apply an excitation magnetic field (e.g., a 335-kHz excitation magnetic field) to deliver power and downlink data. The backscatter receiver equips a pick-up coil to sense the backscattered magnetic field generated by the implantable device 410 and demodulate uplink data. The controller synchronizes the transmitter and the receiver and remotely programs the operation of the implantable device 410 by controlling the generation of the applied magnetic field. In an example, the system may achieve a maximum data rate of 8 kbps in uplink with a 335-KHz frequency of the excitation magnetic field.

Figure 5:
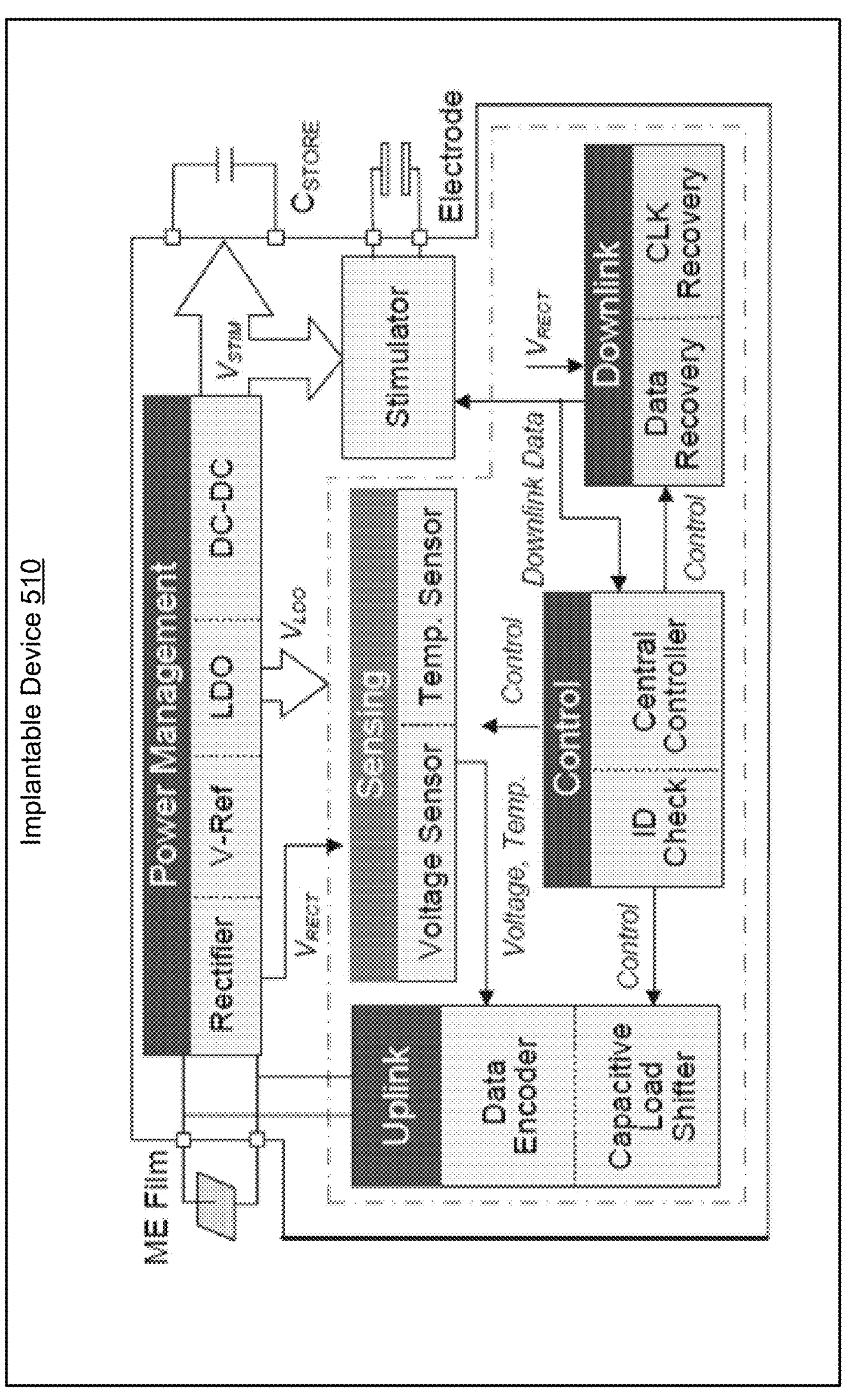
FIG. 5 illustrates exemplary electronics of an implantable device in communication with a base station according to some aspects of the present invention.

FIG. 5 illustrates exemplary electronics of an implantable device 510 in communication with a base station (e.g., base station 110 in FIG. 1) according to some aspects of the present invention. The electronics may be an electrical circuit (e.g., an ASIC) that is coupled to a magnetoelectric film and one or more electrodes. The electrical circuit can provide a variety of functions including power management, bi-directional communication, sensing, and neural stimulation. The implantable device 510 may establish a bi-directional communication with the base station in response to detecting an activation field when the base station is positioned proximate to the implantable device.

In an example, the electrical circuit includes a power management module that interfaces with the magnetoelectric film for energy harvesting and generates supply voltages for the electronics. Alternating current (AC) voltage induced on the magnetoelectric film can be rectified to a DC voltage by an active rectifier. Then the DC voltage can be regulated by a switched-capacitor DC-DC power converter to provide supply voltage for a voltage reference generator and a low-dropout regulator (LDO). The DC-DC converter also charges the off-chip capacitor to buffer energy for high-power stimulation. A constant supply voltage (e.g., 1 V) may be generated by the LDO for low-power digital circuitry.

The implantable device 410 can receive downlink data simultaneously with magnetoelectric power from a base station. Since simultaneous power and data transfers may be constrained by the tradeoff between the power transfer efficiency and bandwidth of the transducer, the downlink data can be modulated by a time-domain scheme, in which multiple bits are encoded into the duration of a single pulse to amortize the low switching speed of the transducer. The data from the base station can be recovered by the electrical circuit through a time-to-digital converter to program its operation and stimulation parameters.

In a particular example, the electrical circuit may sense an implant-received voltage for operation regulation and temperature for in-body thermal monitoring. The voltage sensing can be performed by an 8-bit analog-to-digital converter whose core is a voltage-controlled oscillator (VCO). The VCO's output frequency can lineally change with the implant input voltage. A 16-bit temperature sensor can be implemented by a low power ring-oscillator with a native transistor for local voltage regulation. The temperature sensor can leverage subthreshold oscillation dependence for temperature monitoring with 10-nW power consumption.

An uplink module can transmit the voltage and temperature sensor data to the base station through magnetoelectric backscatter. The electrical circuit modulates the capacitive load on the magnetoelectric film to shift the frequency of the backscattered signal. The uplink module may not include any active-radio components, so its power consumption may be negligible (e.g., <5 nW).

The voltage-controlled stimulation pulses can be generated by a stimulation driver and delivered through the electrodes to target tissue. The stimulation may be performed as an implant stimulation protocol with fully programmable parameters, including amplitude (e.g., 0.2 to 3.5 V, 4 bits), shape (e.g., bi-phasic or mono-phasic), pulse width (e.g., 0.05 to 1.5 ms, 3 bits), and frequency (e.g., 0 to 200 Hz).

Figure 6:
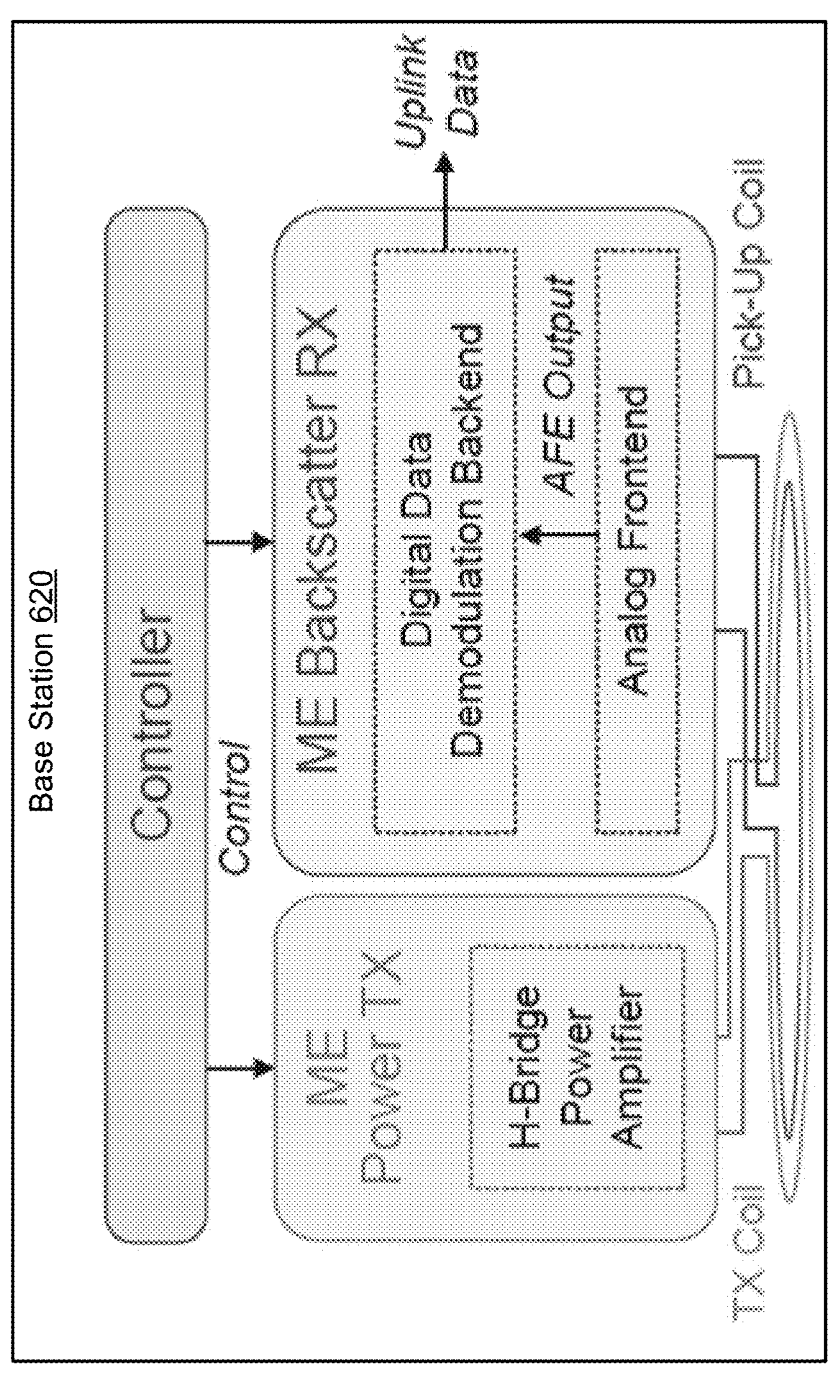
FIG. 6 illustrates exemplary electronics of a base station in communication with an implantable device according to some aspects of the present invention.

FIG. 6 illustrates exemplary electronics of a base station 620 in communication with an implantable device (e.g., implantable device 110 in FIG. 1) according to some aspects of the present invention. The base station 620 includes a magnetoelectric power transmitter, a magnetoelectric backscatter receiver, and a controller. The base station 620 includes a transmitter coil for power and downlink data transfers and a pick-up coil for backscatter sensing.

A magnetic field generator of the base station 620 can include a power amplifier based on an H-bridge that injects AC current into the transmitter coil to produce a magnetic field. In an example, the magnetic field may be 335 kHz. In the backscatter receiver, an analog frontend (AFE) amplifies the magnetoelectric backscattered signal in the pick-up coil and generates recovered pulses for the digital backend for data demodulation. The controller of the magnetic transceiver can control the operations of the base station 620 and the implantable device. To power the implantable device, the controller turns on the power amplifier to apply the alternating magnetic field. By disabling the power amplifier in a short time, the controller generates magnetic field notches to switch the functions of the implantable device, such as communication, sensing, and stimulation. Accordingly, all the components in the system can be synchronized.

In some embodiments, the power amplifier and the AFE can be built with electronic components soldered on printed circuit boards. The data demodulation backend circuit and the control module may be implemented by field programmable gate arrays (FPGA). The AFE for amplification and digitization can be built with an analog multiplexer, an active low-pass filter (LPF), a low-noise instrumentation amplifier, and a high-speed comparator. The voltage of the pick-up coil can be high in the power transfer phase due to strong inductive coupling to the transmitter coil. Thus, the AFE can use a multiplexer with high-voltage tolerance in the input stage to block the input voltage when the applied magnetic field is on. The analog multiplexer can be turned on during the uplink data transmission to pass the backscattered signal sensed by the pick-up coil. High-frequency noise and interference can be filtered out by the LPF, which may use a 375-kHz bandwidth, whose output is amplified by the instrumentation amplifier with a gain of a certain amount (e.g., 60 dB). The comparator can convert the output of the amplifier to a train of digital pulses, whose frequency is substantially similar to the magnetoelectric backscattered field.

The digital backend of the backscatter receiver can employ frequency-to-digital conversion for uplink data demodulation. The digital backend can use several pulses of the output of the AFE to build the demodulation window, transforming the LSK-induced frequency shift a duration of time between the $N_i$th and the $N_j$th AFE output pulse. In an example, $N_i$ can be nine and $N_j$ can be eighteen. A counter can be used to count the number of FPGA clocks in the demodulation window to compute the duration. When the magnetoelectric transducer is connected with a capacitor, the backscattered signal's frequency decreases, resulting in a longer time between the $N_i$th and the $N_j$th AFE output pulse. Hence, by comparing the duration with a predefined threshold, LSK-modulated bits "1" and "0" can be recovered. For example, the predefined threshold may be 27 μs, and the digital backend may determine the length of time it takes for nine frequency pulses. If the nine frequency pulses occur in the backscattered signal data in less than 27 μs, the bit can be set to "0" for the demodulation window, and if the nine frequency pulses occur in the backscattered signal data in more than 27 μs, the bit can be set to "1" for the demodulation window.

III. Exemplary Process

Figure 7:
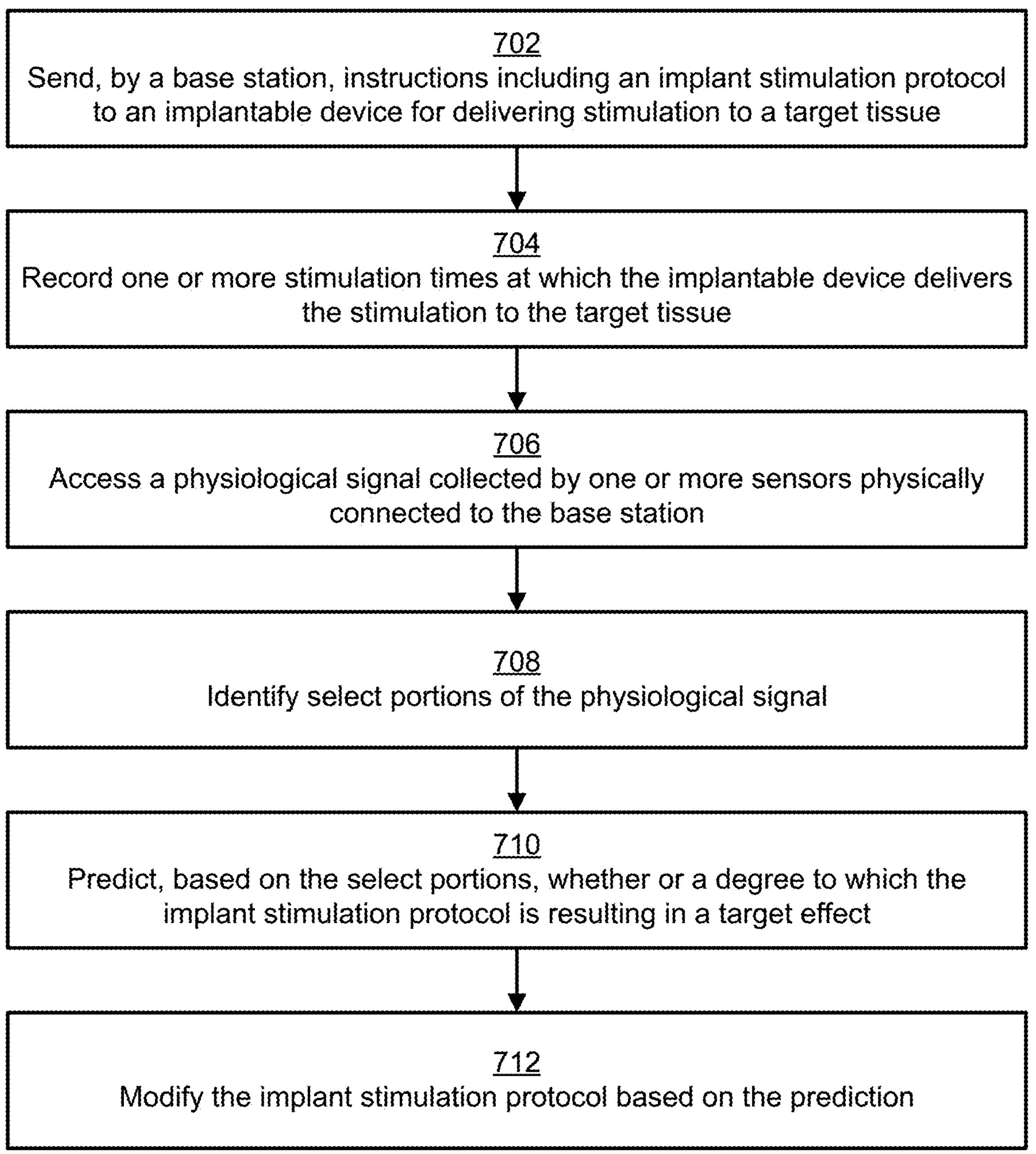
FIG. 7 illustrates a block diagram of a process for wireless power and data transmission of a base station, implantable device, and sensors according to some aspects of the present invention.

FIG. 7 illustrates a block diagram of a process for wireless power and data transmission of a base station, implantable device, and sensors according to some aspects of the present invention. A base station, such as base station 120 in FIG. 1, may perform the steps of FIG. 7. For instance, the base station can include a magnetic field generator, a magnetic transceiver, and electronics for performing the steps of FIG. 7.

At block 702, the base station sends instructions including an implant stimulation protocol to an implantable device for delivering stimulation to a target tissue. The implantable device can be implanted in a brain or at a nerve of a user. The implantable device can include a magnetoelectric film, an electrical circuit coupled to the magnetoelectric film, and one or more electrodes. The implant stimulation protocol may be a default implant stimulation protocol, or the base station may receive an indication of the implant stimulation protocol from a user device associated with a clinician, the user, or other personnel. The implant stimulation protocol may specify an amplitude, frequency, pulse width, shape, etc. of the stimulation that is to be delivered by the implantable device. Upon receiving the instructions, the implantable device can deliver stimulation to the target tissue according to the implant stimulation protocol.

At block 704, the base station records one or more stimulation times at which the implantable device delivers the stimulation to the target tissue. The one or more stimulation times can be indicated in the implant stimulation protocol. So, based on the instructions sent to the implantable device, the base station can record the stimulation times.

At block 706, the base station accesses a physiological signal collected by one or more sensors physically connected or wirelessly connected to the base station. The sensors may be (for example) EEG electrodes, optodes, other signals disclosed herein. At least one of the one or more sensors can be part of a wearable component (e.g., worn around a head, neck, or waist of the user) that also includes the base station. Alternatively or additionally, at least one of the one or more sensors may be connected with, physically attached to and/or part of the implantable device. Each of the one or more sensors can continuously or periodically generate the physiological signal while the base station is proximate the implantable device. So, the physiological signal may include portions during the stimulation delivered by the implantable device and portions when the implantable device does not deliver stimulation. It will be appreciated that a sampling frequency and/or a trigger for sampling may be consistent across multiple or all sensors and/or may differ across at least two (or across all) of the one or more sensors.

At block 708, the base station identifies select portions of the physiological signal. Each portion of the select portions can have a start time corresponding to a stimulation time of the one or more stimulation times. So, the base station can identify start times of the stimulation times based on the implant stimulation protocol and determine which portions of the physiological signal correspond to the start times.

At block 710, the base station facilitates predicting, based on the select portions, whether or a degree to which the implant stimulation protocol is resulting in a target effect. The prediction may be performed by or at the base station, may be performed by or at the implant, may be performed by or at an external device, or may be received from an external device (e.g., a device associated with a caregiver or physician). A particular physiological status (e.g., neural activity, oxygenation level, etc.) indicated by the select portions of the physiological signal may be indicative of the implant stimulation protocol resulting in the target effect. So, if the select portions of the physiological signal indicate the particular physiological status for the user, it can be determined or inferred that the implant stimulation protocol is resulting in the target effect. Otherwise, it can determined or inferred that the implant stimulation protocol is not resulting in the target effect and should be modified.

At block 712, the base station facilitates modifying the implant stimulation protocol based on the prediction. The modification may be identified and/or triggered by or at the base station, may be identified and/or triggered by or at the implant, may be identified and/or triggered by or at an external device, or may be received from and/or triggered by an external device (e.g., a device associated with a care giver or physician). The implant stimulation protocol may be modified based on an input received from the user device associated with a clinician, the user, or other personnel. The input can include an indication of one or more updated stimulation parameters for the implant stimulation protocol. For instance, a new schedule may be set for when the implantable device delivers the stimulation. Additionally or alternatively, the intensity for the stimulation that is generated by the implantable device may be modified. The implant stimulation protocol can also be modified based on a secondary signal that is generated by the implantable device based on backscattering of the stimulation. Portions of the secondary signal that have a start time relative to a stimulation time of the implantable device may be identified and the prediction of whether or the degrsee to which the implant stimulation protocol is resulting in the target effect can be further based on the portions of the secondary signal.

FIG. 7 shows one exemplary process for controlling and monitoring effects of stimulation delivered by an implantable device. Other examples can include more steps, fewer steps, different steps, or a different order of steps.

IV. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

It is claimed:

1. A method, comprising:

sending, by electronics of a base station, instructions including an implant stimulation protocol to each implantable device of a plurality of implantable devices for delivering stimulation to a target tissue, wherein:

each of the plurality of implantable devices includes a magnetoelectric film, an electric circuit coupled to the magnetoelectric film, and one or more electrodes, upon application of an external magnetic field, the plurality of implantable devices are configured to emit a plurality of electric signals with one or more frequencies, the plurality of electric signals with the one or more frequencies overlaps to deliver the stimulation to the target tissue by interference, and the interference is produced by controlling a relative timing of an electrical field generated by the plurality of implantable devices;

receiving, from the plurality of implant devices, a plurality of uplink communication that includes a plurality of identifiers corresponding to the plurality of implantable devices, temperature data and a plurality of recorded stimulation times at which the plurality of implantable devices delivers the stimulation to the target tissue, wherein the plurality of uplink communication is:

performed based on one or more magnetoelectric backscattered signals measured after switching off the application of the external magnetic field, and encoded by modulating the one or more magnetoelectric backscattered signals during a ring-down period, wherein the one or more magnetoelectric backscattered signals are modulated by changing frequency based on the temperature data;

accessing a plurality of physiological signals collected by one or more sensors that are physically connected or wirelessly connected to the base station;

identifying one or more select portions of the each of the plurality of physiological signals, wherein each portion has a start time corresponding to a recorded stimulation time of the plurality of recorded stimulation times;

facilitating a prediction, based on the one or more select portions, one or more portions of the magnetoelectric backscattered signals, the plurality of identifiers and a subset of implantable devices of the plurality of implantable devices having a target effect below a predetermined threshold; and facilitating modifying the implant stimulation protocol, based on the prediction, wherein the modification includes transmitting a new implant stimulation protocol specific to each implantable device of the subset of implantable devices.

2. The method of claim 1, wherein facilitating modifying the implant stimulation protocol includes identifying a new schedule as to when an implantable device delivers stimulation.

3. The method of claim 1, wherein facilitating modifying the implant stimulation protocol includes identifying a new intensity for stimulation that is generated by the implantable device.

4. The method of claim 1, wherein facilitating modifying the implant stimulation protocol includes identifying a duration for which each of one or more stimulations that is generated by the implantable device.

5. The method of claim 1, further comprising:

accessing a secondary signal collected by an input component of the base station; and identifying one or more secondary select portions of the secondary signal, wherein each secondary select portion has a start time relative to a stimulation time of one or more stimulation times;

wherein the prediction of whether or a degree to which the implant stimulation protocol is resulting in the target effect is further based on the one or more secondary select portions.

6. The method of claim 5, the base station includes a magnetic field generation, and wherein the secondary signal was generated based on backscattering of a magnetic field applied by the magnetic field generator of the base station.

7. The method of claim 1, wherein the one or more sensors includes at least one electroencephalography (EEG) electrode.

8. The method of claim 1, wherein the one or more sensors includes a heart-rate monitor, an accelerometer, and/or an optode.

9. The method of claim 1, further comprising:

modulating, by a resonant frequency modulator of the base station, a resonant frequency of the magnetoelectric film by applying different electric loading conditions that change a property of the magnetoelectric film.

10. The method of claim 1, wherein an implantable device is configured to detect an activation field and establish a bi-directional communication link with the base station when the base station is positioned proximate to the implantable device.

11. The method of claim 1, further comprising:

accessing a diagnostic signal of an implantable device during one or more stimulation times at which the implantable device delivers the stimulation to the target tissue; and wherein the modification of the implant stimulation protocol is further based on the diagnostic signal.

12. The method of claim 1, wherein the base station includes a magnetic field generator and a magnetic transceiver.

13. The method of claim 1, further comprising:

receiving a data uplink from an implantable device; and determining one or more recorded stimulation times based on the data uplink.

14. The method of claim 13, wherein the data uplink is in a form of a magnetic field.

15. The method of claim 1, further comprising:

receiving a data uplink from another implantable device; and determining one or more recorded stimulation times based on the data uplink.

16. The method of claim 15, wherein the data uplink is in a form of a magnetic field.

17. A computer-program product tangibly embodied in a non-transitory machine-readable storage medium, including instructions configured to cause one or more data processors to perform a set of actions including:

sending instructions including an implant stimulation protocol to each implantable device of a plurality of implantable devices for delivering stimulation to a target tissue, wherein:

each of the plurality of implantable devices includes a magnetoelectric film, an electric circuit coupled to the magnetoelectric film, and one or more electrodes, upon application of an external magnetic field, the plurality of implantable devices are configured to emit a plurality of electric signals with one or more frequencies, the plurality of electric signals with the one or more frequencies overlaps to deliver the stimulation to the target tissue by interference, and the interference is produced by controlling a relative timing of an electrical field generated by the plurality of implantable devices;

receiving, from the plurality of implant devices, a plurality of uplink communication that includes a plurality of identifiers corresponding to the plurality of implantable devices, temperature data and a plurality of recorded stimulation times at which the plurality of implantable devices delivers the stimulation to the target tissue, wherein the plurality of uplink communication is:

performed based on one or more magnetoelectric backscattered signals measured after switching off the application of the external magnetic field, and encoded by modulating the one or more magnetoelectric backscattered signals during a ring-down period, wherein the one or more magnetoelectric backscattered signals are modulated by changing frequency based on the temperature data;

accessing a plurality of physiological signals collected by one or more sensors that are physically connected or wirelessly connected to a base station;

identifying one or more select portions of the each of the plurality of physiological signals, wherein each portion has a start time corresponding to a recorded stimulation time of the plurality of recorded stimulation times;

facilitating a prediction, based on the one or more select portions, one or more portions of the magnetoelectric backscattered signals, the plurality of identifiers and a subset of implantable devices of the plurality of implantable devices having a target effect below a predetermined threshold; and facilitating modifying the implant stimulation protocol, based on the prediction, wherein the modification includes transmitting a new implant stimulation protocol specific to each implantable device of the subset of implantable devices.

18. The computer-program product of claim 17, wherein facilitating modifying the implant stimulation protocol includes identifying a new schedule as to when an implantable device delivers stimulation.

19. The computer-program product of claim 17, wherein facilitating modifying the implant stimulation protocol includes identifying a new intensity for stimulation that is generated by the implantable device.

20. The computer-program product of claim 17, wherein facilitating modifying the implant stimulation protocol includes identifying a duration for which each of one or more stimulations that is generated by the implantable device.

21. A system comprising:

one or more processors;

one or more non-transitory computer-readable media storing instructions, which, when executed by the system, cause the system to perform a set of actions comprising:

sending instructions including an implant stimulation protocol to each implantable device of a plurality of implantable devices for delivering stimulation to a target tissue, wherein:

each of the plurality of implantable devices includes a magnetoelectric film, an electric circuit coupled to the magnetoelectric film, and one or more electrodes, upon application of an external magnetic field, the plurality of implantable devices are configured to emit a plurality of electric signals with one or more frequencies, the plurality of electric signals with the one or more frequencies overlaps to deliver the stimulation to the target tissue by interference, and the interference is produced by controlling a relative timing of an electrical field generated by the plurality of implantable devices;

receiving, from the plurality of implant devices, a plurality of uplink communication that includes a plurality of identifiers corresponding to the plurality of implantable devices, temperature data and a plurality of recorded stimulation times at which the plurality of implantable devices delivers the stimulation to the target tissue, wherein the plurality of uplink communication is:

performed based on one or more magnetoelectric backscattered signals measured after switching off the application of the external magnetic field, and encoded by modulating the one or more magnetoelectric backscattered signals during a ring-down period, wherein the one or more magnetoelectric backscattered signals are modulated by changing frequency based on the temperature data;

accessing a plurality of physiological signals collected by one or more sensors that are physically connected or wirelessly connected to a base station;

identifying one or more select portions of the each of the plurality of physiological signals, wherein each portion has a start time corresponding to a recorded stimulation time of the plurality of recorded stimulation times;

facilitating a prediction, based on the one or more select portions, one or more portions of the magnetoelectric backscattered signals, and the plurality of identifiers and a subset of implantable devices of the plurality of implantable devices having a target effect below a predetermined threshold; and facilitating modifying the implant stimulation protocol, based on the prediction, wherein the modification includes transmitting a new implant stimulation protocol specific to each implantable device of the subset of implantable devices.

22. The system of claim 21, wherein facilitating modifying the implant stimulation protocol includes identifying a new schedule as to when an implantable device delivers stimulation.

23. The system of claim 21, wherein facilitating modifying the implant stimulation protocol includes identifying a new intensity for stimulation that is generated by the implantable device.

24. The system of claim 21, wherein facilitating modifying the implant stimulation protocol includes identifying a duration for which each of one or more stimulations that is generated by the implantable device.

* * * * *